United States Patent [19]

Smith

[11] Patent Number: 4,730,050
[45] Date of Patent: Mar. 8, 1988

[54] NOVEL ENZYME DERIVATIVES

[75] Inventor: Richard A. G. Smith, Reigate Surrey, England

[73] Assignee: Beecham Group p.l.c., England

[21] Appl. No.: 34,784

[22] Filed: Apr. 3, 1987

Related U.S. Application Data

[60] Continuation of Ser. No. 785,012, Oct. 7, 1985, abandoned, which is a division of Ser. No. 684,359, Dec. 21, 1984, Pat. No. 4,600,580.

[30] Foreign Application Priority Data

Dec. 24, 1983 [GB] United Kingdom ............... 8334499

[51] Int. Cl.$^4$ .................... A61K 37/48; C07C 103/52; C07G 7/00; C12N 9/70
[52] U.S. Cl. .................................. 546/290; 546/292; 546/294; 548/541; 548/542; 548/543; 548/545; 548/546; 548/547; 548/551; 260/349; 424/94.3; 435/181; 436/532
[58] Field of Search ...................... 546/290, 292, 294; 548/541, 542, 543, 545, 546, 547, 551; 260/349; 436/532; 435/181; 424/94

[56] References Cited

U.S. PATENT DOCUMENTS

| 4,085,005 | 4/1978 | Bleha et al. | 436/532 |
| 4,177,038 | 12/1979 | Biebricher et al. | 435/181 |
| 4,267,273 | 5/1981 | Smith | 435/181 |
| 4,285,932 | 8/1981 | Smith | 435/181 |
| 4,286,964 | 9/1981 | Seed | 436/532 |
| 4,287,345 | 9/1981 | Kotani et al. | 435/181 |
| 4,412,000 | 10/1983 | Lehmann et al. | 435/181 |
| 4,429,008 | 12/1984 | Martin et al. | 436/532 |
| 4,569,789 | 2/1986 | Blattler et al. | 424/85 |

FOREIGN PATENT DOCUMENTS

| 009879 | 4/1980 | European Pat. Off. | |
| 0041766 | 12/1981 | European Pat. Off. | |
| 091240 | 10/1983 | European Pat. Off. | |
| 0152736 | 8/1985 | European Pat. Off. | 435/181 |

OTHER PUBLICATIONS

Moroi et al., Chem. Abst. 87: 34998t (1977).
Waller et al., Chem. Abst. 99: 156039z (1983).

Primary Examiner—Delbert R. Phillips
Assistant Examiner—Nathan M. Nutter
Attorney, Agent, or Firm—Jacobs & Jacobs

[57] ABSTRACT

A derivative of a fibrinolytic enzyme in which the catalytic site on the enzyme which is responsible for fibrinolytic activity is blocked by a human protein attached thereto by way of a reversible linking group.

9 Claims, 5 Drawing Figures

NOVEL ENZYME DERIVATIVES

CROSS-REFERENCE

This is a continuation of my copending application, Ser. No. 785,012, filed Oct. 5, 1985, now abandoned, which was a division of my then copending application Ser. No. 684,359, filed Dec. 21, 1984, now U.S. Pat. No. 4,600,580, issued July 15, 1986.

This invention relates to enzyme derivatives for use in the treatment of thrombotic diseases.

European Pat. No. 0,009,879 discloses derivatives of in vivo fibrinolytic enzymes which are useful therapeutic agents for treating venous thrombosis. The derivatives are characterised by the active catalytic site on the enzymes being blocked by a group which is removable by hydrolysis such that the pseudo first order rate constant for hydrolysis is in the range $10^{-6} \text{sec}^{-1}$ to $10^{-3} \text{sec}^{-1}$.

It has now been found that certain human proteins may be chemically modified so that they can function as removable blocking groups in the sense used in the above mentioned European Patent, and that these groups, when linked to enzymes, can produce enzyme derivatives with slow physiological clearance rates.

According to the present invention there is provided a derivative of a fibrinolytic enzyme in which the catalytic site on the enzyme which is responsible for fibrinolytic activity is blocked by a human protein attached thereto by way of a reversible linking group.

As used herein the expression "reversible linking group" includes groups which are removable by hydrolysis at a rate such that the pseudo first order rate constant for hydrolysis is in the range $10^{-6} \text{sec}^{-1}$ to $10^{-3} \text{sec}^{-1}$ in the isotonic aqueous media at pH 7.4 at 37° C.

The preferred rate constant is in the range $1 \times 10^{-5} \text{sec}^{-1}$ to $8 \times 10^{-4} \text{sec}^{-1}$.

Suitably the catalytic site on the enzyme is blocked by group of structure (I)

$$P—B—A—X \qquad (I)$$

in which
P is a human protein modified by treatment with an amino acid side chain specific reagent to include a protein attachment group, X is an acyl group of formula

in which R is an aromatic or aliphatic residue, A is a bridging group comprising at least one hetero atom selected from oxygen, sulphur and nitrogen, in which the nitrogen is optionally substituted by $C_{1-6}$ alkyl, B is a linear hydrophilic linking group, linked to the protein attachment group on P.

Figure 1:
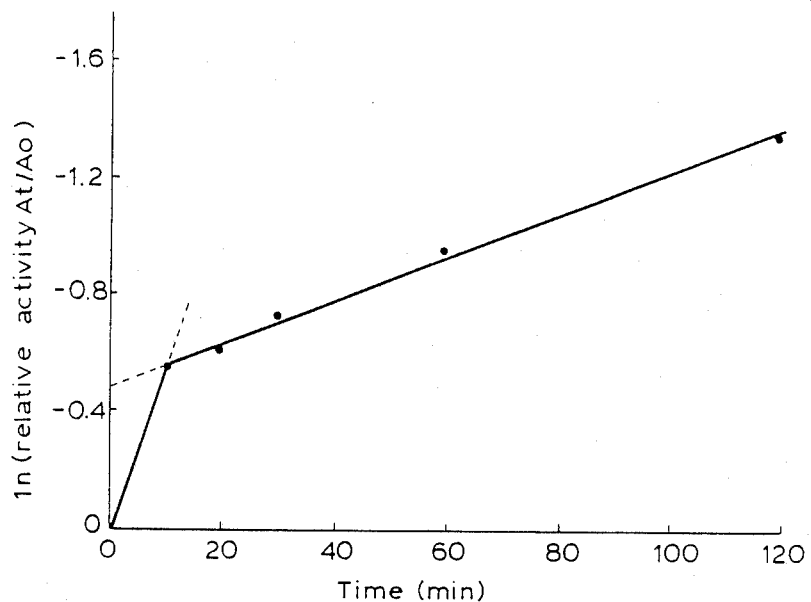
FIG. 1 illustrates the formation of the albumin-t-PA conjugate of Example 4.

The term 'fibrinolytic enzyme' is used herein to mean any enzyme which demonstrates in vivo fibrinolytic activity as defined in the above mentioned European Patent, and includes enzymes which are obtainable from mammalian urine, blood or tissues, or from bacteria expressing genes specifying such mammalian enzymes and which can activate plasminogen. An example of tissue-type plasminogen activator (t-PA) is melanoma plasminogen activator, the extraction of which is described in Published European Patent Application No. 41766. t-PA is a type of activator known as human extrinsic plasminogen activator. Intrinsic plasminogen activators, such as urokinase and plasmin, are also suitable fibrinolytic enzymes for use in the present invention.

Examples of suitable human proteins are human plasma proteins known to have slow physiological clearance rates such as human serum albumin (and its oligomers), immunoglobulin, human fibrinogen and human plasminogen. Preferably the protein has a molecular weight in the region of 30,000 to 800,000 daltons. Preferred proteins are ones which are known to have significant affinity for components of a thrombotic mass, for example, human plasminogen. Optionally, the protein may itself be a fibrinolytic enzyme as hereinbefore defined such as urokinase or tissue plasminogen activator, or a proenzyme thereof such as prourokinase. When the protein is a fibrinolytic enzyme, the active catalytic site thereof may optionally be blocked as described in European Patent No. 0009 879. An example of such a blocked fibrinolytic enzyme is p-aminobenzoyl urokinase.

Examples of derivatives of the invention include

| | |
|---|---|
| human serum albumin → | human tissue plasminogen activator |
| human serum albumin → | urokinase |
| urokinase or acylated urokinase → | human plasmin |
| human tissue plasminogen activator → | human plasmin |
| human immunoglobulin G → | human tissue plasminogen activator |
| human plasminogen → | human tissue plasminogen activator | where→represents a reversible linkage to the active centre of the enzyme.

Examples of suitable groups X include groups derived from those blocking groups described in European Pat. No. 0,009,879. Preferred groups are optionally substituted benzoyl groups as described in the above mentioned European Patent further substituted at the 2 or 4 position by the group A, and optionally substituted acryloyl groups also described in the above mentioned European patent and joined to A at the 2 or 3 position thereof.

Suitable groups A are those which provide sufficient stabilisation of the resulting benzoyl or acryloyl-enzyme to result in a pseudo first order rate constant for hydrolysis in the above mentioned range and preferably in the range $1 \times 10^{-5}$ to $8 \times 10^{-4} \text{sec}^{-1}$.

Examples of A are:

  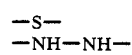

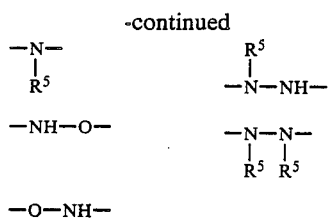

wherein $R^5$ is a $C_{1-6}$ alkyl group.

The protein attachment group is a functionality derived by modification of the protein with a reagent specific for one or more amino acid side chains, and which contains a group capable of reacting with a group B.

Examples of groups B are substituted $C_2$-$C_{10}$ alkanes such as 6-aminohexyl, or linear polymers such as polyethylene glycol, polypropylene glycol, poly-glycine, poly-alanine or poly-sarcosine. The linear group B may optionally contain a cleavable section to facilitate analysis of the derivative or to react with the protein attachment group such as those derived from a 3-thio propionyl or 2-thio acetyl derivative of the ω-amino alkane or polymer function. An example of a cleavable section is a disulphide bond. Preferably the disulphide bond is derived from reaction of P with the linear group B and thus is generated at the linkage of B with P. Alternatively the cleavable section may comprise an α, β dihydroxy function.

Suitably B is a group; $-S(CH_2)_2CONH-$, $-S-(CH_2)_2CONH(CH_2)_6-$ or $-S-(CH_2)_2CONH(CH_2)_2-$ As an example, the generation of a free thiol function by reaction of the protein with 2-iminothiolane or N-acetyl homocysteine thiolactone will permit coupling of the protein attachment group with a thiol-reactive B structure. Alternatively, the protein attachment group can contain a thiol-reactive entity such as the 6-maleimidohexyl group or a 2-pyridyl-dithio group which can react with a free thiol in B. Preferably, the protein attachment group is derived from protein modifying agents such as 2-iminothiolane that react with lysine ε-amino groups in proteins.

The derivatives of the present invention may be prepared by reacting together a human protein optionally modified to include a protein attachment group, a fibrinolytic enzyme and a linking agent having a moiety capable of reacting with the catalytic site of the enzyme and a moiety capable of reacting with a protein amino group or protein attachment group to form a reversible linking group as hereinbefore defined.

In particular the derivatives may be prepared by treating a human protein, which has been optionally modified by treatment with an amino acid side chain specific reagent to include a protein attachment group, with an acylating agent of formula (II)

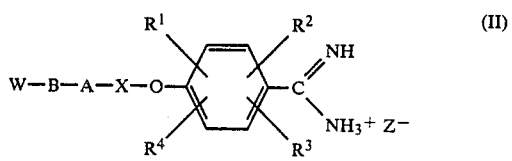

in which B, A and X are as defined with reference to formula (I),

W represents a group capable of reacting directly with the amino acid side chain of a protein or, when the protein includes a protein attachment group, W represents a group capable of reacting with the attachment group, Z represents a counter anion, preferably halide or p-toluenesulphonate, and each of $R_1$ to $R_4$ represents hydrogen or an electron withdrawing moiety which increases the reactivity of an amidinophenyl ester; and reacting the acylated protein produced thereby with a fibrinolytic enzyme.

The acylating agents of formula (II) are novel and as such form part of the invention.

When W represents a group capable of reacting directly with the amino acid side chain of a protein, it is preferably an N-succinimidyl group. When W represents a group capable of reacting with a protein attachment group, it is preferably a pyridylthio group. Optionally W may be a photoactivated group such as 2-nitro-4-azido phenyl.

Preferably, each of $R^1$ to $R^4$ represents hydrogen or halogen.

The derivatives of the present invention may also be prepared by treating a human protein, which has been modified by treatment with an amino acid side chain specific reagent to include a protein attachment group, with a fibrinolytic enzyme which itself has been modified by treatment with an acylating agent of formula (II) in which W is a group capable of reacting with the protein attachment group on the protein.

Preferably, W is a pyridylthio group.

In the above processes, modification of the protein to introduce a protein attachment group is preferably carried out in aqueous buffered media at a pH between 3.0 and 9.0 depending on the reagent used. For a preferred reagent, 2-iminothiolane, the pH is preferably 6.5–8.5. The concentration of protein is preferably high (>10 mg/ml) and the modifying reagent is used in a moderate (1.1- to 5-fold) molar excess, depending on the reactivity of the reagent. The temperature and duration of reaction are preferably in the range 0°–40° C. and 10 minutes to 7 days. The extent of modification of the protein may be determined by assaying the protein attachment groups introduced.

Such assays may be standard protein chemical techniques such as titration with 5,5'-dithiobis-(2-nitrobenzoic acid). Preferably, 0.5–2.0 moles of protein attachment group will be introduced on average per mole of protein. The modified protein may be separated from excess modifying agents by standard techniques such as dialysis, ultrafiltration, gel filtration and solvent or salt precipitation. It is generally desirable to react to modified protein with the acylating agent or the acylated fibrinolytic enzyme as soon as possible, but in certain cases, the intermediate material may be stored in frozen solution or lyophilised.

The modified protein prepared as deseribed above may be reacted with the acylating agent of formula (II) under conditions similar to those used for the initial introduction of the protein attachment group but with the following qualifications:

(a) To avoid hydrolysis of the amidinophenyl ester, the preferred pH range is 7.0 to 8.0 and non-nucleophilic buffers should be used.

(b) The preferred temperature range is 0°–30° C. and the duration of reaction up to 6 hours.

(c) The molar ratio of acylating agent to protein attachment group is preferably in the range 1 to 10.

(d) The reaction may, optionally, be monitored by observing the release of a derivative of group W (e.g. pyridine 2-thione).

(e) Because of the reactivity of the product (a proteinaceous acylating agent), it is desirable to separate the product from the excess acylating agent of formula (II) as quickly as possible. For this purpose, high performance size exclusion chromatography or diafiltration may be used.

(f) The product should preferably be reacted with the fibrinolytic enzyme immediately but may be stored in frozen solution (not lyophilised) below $-40°$ C. for short periods.

The treatment of an unmodified protein with an acylating agent of formula (II) is generally performed under conditions similar to those used for the introduction of a protein attachment group. However, the reactivity of this type of reagent requires that precautions similar to those noted in paragraphs (a) to (f) above should be exercised.

Where the modified protein itself comprises a fibrinolytic enzyme whose active catalytic site is blocked, the blocking may be carried out as described in European Patent No. 000 9879 either before or after modification as described above, or after reaction with the fibrinolytic enzyme.

In the process aspect of the invention which utilises a reaction between modified protein and acylated fibrinolytic enzyme, the enzyme may first be reacted with an acylating agent of formula (II) under the conditions described for the introduction of blocking groups in European Published Patent Application No. 0,009,879. Having been freed of excess reagent by the techniques noted above, the acylated enzyme may then be reacted with protein containing a protein attachment group under conditions similar to those used in paragraphs (a) to (d) above. However, it is preferable to conduct the coupling below 10° C. (preferably 0°-4° C.) in order to minimise the hydrolysis of the acylated enzyme. In addition, the modified protein may be used in a large molar excess (up to $10^4$-fold) over the acylated enzyme. The latter conditions also apply to the coupling between an a proteinaceous acylating agent and fibrinolytic enzyme.

The derivatives of this invention may be purified from excess modified protein/protein acylating agent and uncoupled enzyme by a variety of separation techniques. Because the molecular weight of the derivative will usually be significantly greater than that of its components, rapid size fractionation methods such as protein high performance gel chromatography are particularly advantageous. In addition, affinity chromatography utilising an insoluble matrix with affinity for the fibrinolytic enzyme component, may be used, in conjugation with gel filtration methods.

The acylating agents of formula (II) may be prepared by a variety of standard procedures. A preferred general synthetic route is given below.

(a) Reaction of an acylating agent containing a masked reactive functionality (for example, N-succinimidyl-3-(2-pyridyldithio)propionate-SPDP) with a 2- or 4-substituted benzoic acid derivative containing a nucleophilic function on the substituents (for example: 4-hydrazinobenzoic acid, N-2(6-aminohexyl)aminobenzoic acid or N-4(2-aminoethyl)aminobenzoic acid). Preferred reaction conditions require dry pyridine (or another basic solvent) at ambient temperature for 1-24 hours. (b) The intermediate acid from (a) is esterified with a salt of 4-amidinophenol (or a ring-substituted derivative thereof) using dicyclohexylcarbondiimide in a weakly basic solvent as described for simple blocking agents in European Published Patent No. 0,009,879. It is preferable to use a slight molar excess of the amidinophenol (1.5 to 4-fold) to ensure efficient esterification. Optionally, the esterification may be performed in the presence of anhydrous p-toluenesulphonic acid as an acidic catalyst.

The derivatives of this invention are preferably administered as pharmaceutical compositions.

Accordingly, the present invention also provides a pharmaceutical composition comprising the derivative of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubilising agent to keep the derivative in solution and a local anaesthetic such a lignocaine to ease pain at the site of injection. Generally, the derivative will be supplied in unit dosage form for example as a dry powder or water-free concentrate in a hermetically sealed container such as an ampoule or sachette indicating the quantity of enzyme conjugate in activity units, as well as an indication of the time within which the free, unmodified protein will be liberated. Where the derivative is to be administered by infusion, the derivative will be dispensed with an infusion bottle containing sterile pharmaceutical 'water for injection'. Where the derivative is to be administered by injection the derivative is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature thrombus will generally receive a daily dose of from 0.10 to 2.0 mg/kg$^{-1}$ of body weight either by injection in up to five doses or by infusion. For the treatment of coronary thrombosis a similar dose may be given as a single intravenous bolus.

No toxic effects have been observed with the compounds of the invention within the above described dosage range.

Accordingly, in a further aspect of the invention there is provided a method of treating thrombotic disorders, which comprises administering to the sufferer an effective non-toxic amount of a derivative of the invention. The following Methods and Examples illustrate the invention.

METHODS (a) Chromogenic substrate assay

Urokinase and t-PA were assayed against the chromogenic substrates (KabiVitrum, Sweden) S-2444 and S-2288, respectively at a substrate concentration of 1 mM in 0.1M triethanolamine.HCl pH 8.0 at 250° C. An SU is defined as the amount of activity that gives an O.D. increase of 0.001/min in 1ml substrate in a 1 cm pathlength cell.

(b) Rate constant determinations

The pseudo first order rate constant is determined by hydrolysing the acyl-enzyme under physiological conditions, i.e. in isotonic aqueous media at pH 7.4 and at 37° C. At regular intervals aliquots are withdrawn and incubated with a chromogenic substrate and the rate of conversion of the substrate measured as indicated above.

The hydrolysis is followed until such time as the rate of conversion of substrate reaches a maximum. The rate constant k is then calculated by plotting:

$$\log_e (1 - A^t/A_{max}) \text{ against } t$$

where $A_{max}$ is the maximum rate at which an aliquot converts substrate and $A_t$ is the rate at which an aliquot converts substrate at time t.

(c) Assay of fibrinolytic activity in the bloodstream of rats

Male Sprague-Dawley rats (300–400 g) were anaesthetized with pentobarbitone sodium (60 mg/kg i.p.). One carotid artery was cannulated for collection of blood samples. One femoral vein was cannulated for injection of heparin (50 U/kg) and compound under test. Approximately 5 min after heparinization, a pre-dose blood sample (0.8 ml) was taken and mixed with 0.1 volumes 129 mM trisodium citrate. The compound under test was then injected (1 ml/kg) over 10 s. Further blood samples were taken exactly 1, 2, 4, 8, 16, 30 and 60 min later. Heparin treatment (50 U/kg) was repeated after the 30 min sample to maintain cannula patency. All citrated blood samples were kept on ice until the end of each experiment, then centrifuged at 1700 g for 15 min at 4° to obtain plasma. The euglobulin fraction was precipitated by adding 0.1 ml each plasma to 1.82 ml ice-cold 0.011% (v/v) acetic acid in water. After 30 min standing in ice, all tubes were centrifuged at 1700 g for 15 min at 4°. The supernatants were poured away, the inner walls of each tube carefully wiped dry and each precipitate redissolved in 0.4 ml 0.1M triethanolamine HCl buffer, pH 8.0, containing 0.05% (w/v) sodium azide. Aliquots (20 µl) were then applied to fibrin plates in quadruplicate. Fibrin plates were prepared from 0.4% (w/v) human fibrinogen (Nabi, Grade 1, Flow Laboratories, Scotland) dissolved in 0.029M barbitone in 125 mM NaCl, pH 7.4, pipetted (9 ml) into 10×10 cm square plastic dishes (Sterilin) and clotted by rapid mixing with 0.3 ml bovine thrombin (50 NIH units/ml, Parke-Davis, UK). Plates were incubated at 37° for 18-24 h usually, but longer if required, and stained with aqueous bromophenol blue. For each lysis zone, two diameters perpendicular to each other were measured using Vernier calipers. All diameters for each sample were averaged, and this mean converted to fibrinolytic activity by reference to a calibration curve. The latter was obtained by adding known amounts of the compound under test to a stock of plasma pooled from at least ten rats. These standards were processed using the same methods and at the same time as the experimental samples. To construct the calibration curve, diameters (mm) were plotted against $\log_{10}$ concentration of compound. The plasma concentration of compound in each experimental sample was expressed as a percentage of that expected on the basis of the dose given and the assumption of 35 ml plasma/kg body weight for each rat.

(d) Assay of [$^{125}$I]-labelled conjugates in the bloodstream of rats

Aliquots (100 µl) of citrated blood were mixed with 20 µl 1% NaI and 400 µl 20% trichloroacetic acid (TCA) to precipitate protein-bound $^{125}$I. After 30 min on ice, the blood was centrifuged and both supernatant and precipitate counted for $^{125}$I-content. The percentage total counts in the precipitate was calculated to give TCA-precipitable counts. For each conjugate, the radiometric clearance pattern was obtained by plotting TCA-precipitable counts (as % of theoretical) in the blood against time.

(e) Assay of fibrinolytic activity in the bloodstream of guinea pigs

Male Dunkin Hartley guinea pigs (350–450 g) were anaesthetized with urethane (25% w/v solution; 6 ml/kg i.p.). One carotid artery was cannulated for collection of blood samples. One femoral vein was cannulated for injection of heparin (50 U/kg i.v.) and compound under test. Approximately 5 min after heparinization, a pre-dose blood sample (2 ml) was taken and mixed with 0.1 volumes 129 mM trisodium citrate. The compound under test was then injected (1 ml/kg) over 10 s. Further blood samples were taken exactly 2, 4, 8, 16, 30, 60 and 90 min later. Heparin treatment (50 U/kg i.v.) was repeated after the 30 min sample to maintain cannula patency. All citrated blood samples were kept on ice until the end of each experiment, then centrifuged at 1700 g for 15 min at 4° to obtain plasma. Each plasma sample was diluted 200-fold in phosphate buffered saline, pH 7.4, containing 0.01% (v/v) Tween 80. Aliquots (30 µl) were then applied to fibrin plates in quadruplicate. Fibrin plates were prepared from 0.4% (w/v) human fibrinogen (Kabi, Grade L, Flow Laboratories, Scotland) dissolved in 0.029M barbitone in 125 mM NaCl, pH 7.4, pipetted (10 ml) into 10×10 cm square plastic dishes (Sterilin) and clotted by rapid mixing with 0.3 ml bovine thrombin (50 NIH units/ml, Parke-Davis, U.K.). Plates were incubated at 37° for 18-24 h usually, but longer if required, and stained with aqueous bromophenol blue. For each lysis zone, two diameters perpendicular to each other were measured using Vernier calipers. All diameters for each sample were averaged, and this mean converted to fibrinolytic activity by reference to a calibration curve. The latter was obtained by adding known amounts of the compound under test to the pre-dose plasma of each animal. These standards were processed using the same methods and at the same time as the experimental samples. To construct the calibration curve, diameters (mm) were plotted against $\log_{10}$ concentration of compound. The plasma concentration of compound in each experimental sample was expressed as a percentage of that expected on the basis of the dose given and the assumption of 50 ml plasma/kg body weight for each guinea pig.

EXAMPLE 1

(a)

4-[N-2-(3-[2-pyridyl]dithiopropionyl)hydrazino]benzoic acid

SPDP (100 mg, 0.32 mmol) was dissolved in dry pyridine (1.0 ml) and 4-hydrazino benzoic acid (55 mg 0.32 mmol) added. The mixture was warmed to 56° C. for 4 h and left at ambient temperature overnight. The product was evaporated to to dryness and the resulting yellow oil recrystallised from water (6.0 ml) and EtOH (0.5 ml). A gummy solid was deposited on cooling and this was dissolved in ethanol (1.0 ml), evaporated and dried in vacuo to give a glassy solid.

Yield: 72.6 mg (65%). NMR (MeOH-D$^4$). δ: 8.05, irr d, 1H, Pyridine H6. 7.50, overlapping dd, 4H, Pyridine H3+4,+benzoyl A$_2$B$_2$ qt. 6.9, Qunit, 1H, Pyridine H5. 6.45 d, 2H, benzoyl A$_2$B$_2$. 2.6M. 4H. —CH$_2$CH$_2$—. Anal: C$_{13}$H$_{20}$N$_2$O$_2$ (236.37) requires: C: 66.07, H: 8.53, N: 11.85. Found: C: 66.04, H: 8.16, N: 10.62.

(b)
4-[N-2-(3-[2-pyridyl]dithiopropionyl)hydrazino]benzoic acid 4'-amidinophenyl ester.HCl The above acid (0.21 mmol) was dissolved in warm (30° C.) dry pyridine (1.0 ml) containing 4-amidinophenol.HCl (144 mg, 0.83 mmol) and N,N dicyclohexyl carbodiimide (48 mg, 0.21 mmol). The mixture was left at ambient temperature for 48 h and then filtered, washing with dry pyridine. The filtrates were evaporated to dryness and the solid triturated with H$_2$O (10 ml) and saturated brine (1.0 ml). The solid was recrystallized from EtOH: Et$_2$O 1:1 v/v (5.0 ml) with addition of the further ether. The resulting gum was dried in vacuo and then recrystallised from EtOH: H$_2$O 1:9 v/v (4 ml) with addition of brine (0.5 ml) to the filtrate. The yellow solid was dried in vacuo over P$_2$O$_5$.

yield: 52.4 mg (52%). M.P. 140°–142° C. NMR (DMSO-d$^6$). δ: 10.15, 5, 1H, Amide H. 9.35/9.55 d, 4H, Amidine H, 8.5 irr m. Pyridine H. 7.9/7.5, 7.3/6.8 irr d. Aromatic H, 3.15 d, 2H, CH$_2$, 2.75 d, 2H, CH$_2$.

Reduction of the material with 1 mN dithiothreitol at pH 7.4 and monitoring of pyridine 2-thione release at 343 nM indicated a purity of about 70%.

EXAMPLE 2

(a) N-6-(aminohexyl)anthranilic acid 2-chlorobenzoic acid (31.4 g, 0.2 mol), 1.6 diaminohexane (55.7 g, 0.5 mol) anhydrous potassium carbonate (25.6 g), n-pentanol (68 ml) and copper powder (0.3 g) were refluxed for 5 h. n-pentanol and 1,6 diaminohexane were distilled off and the residue poured into cold water (1.5 l). The mixture was acidified to pH 7.0 with concentrated HCl and cooled to 4° C. The resulting gum was taken up in hot H$_2$O: EtOH conc. HCl 8:8:1 v/v (850 ml), cooled, filtered and brought to pH 7.0 with 5N NaOH. The precipitate was dissolved in H$_2$O: conc. HCl 1:1 v/v (80 ml), diluted to 300 ml with H$_2$O and with 5N NaOH. A yellow solid was precipitated at 4° C., filtered and dried in vacuo (5 ml).

Yield: 24.4 g (52%. M.P. 192° C. (dec). NMR (DCl/D$_2$O). δ: 8.20, M, 1H, Anthraniloyl H6. 7.65M, Anthroniloyl H3+4+5. 3.50 t, 2H, Aminomethylene. 3.00, t, 3H Aminomethylene. 1.4–2.0, broad envelope. 8H backbone CH$_2$ (b)
N-(6-[3-(2-pyridyl)dithiopropionyl]aminohexyl)anthranilic acid 4'-amidinophenyl ester.HCl SPDP (200 mg, 0.64 mmol) was dissolved in dry pyridine (1.0 ml) and added to the above aminohexyl anthranilic acid (151 mg, 0.64 mmol) which rapidly dissolved. The solution was allowed to stand at ambient temperature for 4 h and then evaporated under reduced pressure. The resulting oil was dissolved in hot 1M HCl (5 ml) and the solution neutralised with 5M NaOH (0.5 ml), then allowed to cool overnight at 4° C. A pale yellow solid was precipitated and isolated by decantation of the supernatant and drying of the residue over P$_2$O$_5$ in vacuo. The product was dissolved in dry pyridine (1.0 ml) and p-amidinophenol. HCl (221 mg, 1.28 mmol) and anhydrous p-toluenesulphonic acid (100 mg) added, followed by N,N dicylohexylcarbodiimide (158 mg, 0.77 mmol). The mixture was stirred overnight at ambient temperature and filtered, washing with dry pyridine (3.0 ml). Combined filtrates were evaporated under reduced pressure to an oil which was recrystallised twice from 20% v/v ethanol/water Yield: 154 mg (30%). M.P. approx. 70° C. (glass transition). NMR (DMSO-d$^6$, 270 MHz). δ: 9.165/9.436, d, 4H, Exch.D$_2$O amidine H. 8.056/8.021, dd, 1H, Pyridine H6. 7.95/7.92 and 7.52/7.51, Qt, 4H. Amidinophenol H. 7.6–7.85, M, 2H, Pyridine H4+H5. 7.48–7.55, M, 2H, Pyridine H3+amide NH. 7.21–7.25, M, 1H, anthraniloyl H4. 7.11–7.14, 1H, anthraniloyl H2. 6.82–6.86, d, 1H, anthraniloyl$_O$H5. 6.67–6.70, d, 1H, anthraniloyl H3. 3.37, M, 2H,$_o$CH$_2$—C—NH. 3.20–3.22, d, 2H, —CH$_2$—S—. 3.00–3.04, M, 2H, C—NHCH$_2$. 2.48–2.51, M, 2H, —CH$_2$NH—. 1.32–1.61, 2 multiplets. 8H, —(CH$_2$)$_4$—.

The NMR spectrum also indicated the presence of approximately 0.5 mol of solvent ethanol and 0.7 mol of p-toluenesulphonate ion per mol of product.

Reduction of the material with dithiothreitol at pH 7.4 and monitoring of the pyridine 2-thione release at 343 nm indicated a purity of about 64%.

EXAMPLE 3

Preparation of substituted amidinophenyl esters of N-4-{N-2-[3-(2-pyridyldithio)propionyl]aminoethyl-}amino benzoic acid (a) t-butyl 4-aminobenzoate 4-Aminobenzoic acid (5.0 g) was suspended in thionyl chloride (50 ml) and heated to a gentle reflux. After two hours the solution went completely clear, and so the reaction was allowed to cool and the thionyl chloride was removed under reduced pressure, the last traces by azeotrope with dichloromethane (3×50 ml). The resulting acid chloride was dissolved in more dichloromethane (50 ml) and a solution of t-butanol (15 ml) in dichloromethane (15 ml) was added to the stirred solution which was cooled in an ice bath. A solid white precipitate was formed—the hydrochloride salt of the title compound. This was isolated by evaporation of the dichloromethane, followed by suspension of the solid in ethyl acetate (100 ml) and filtration. The material was suspended in 10% aqueous sodium hydrogencarbonate solution (100 ml) and extracted into dichloromethane (3×100 ml). The organic layer was dried, filtered and evaporated to leave a pale cream solid (4.67 g, 66%), m.p. 106°–109° C. (lit. m.p. 109.5° C.) (R. Adams et al (1926) J. Amer. Chem. Soc., 48, 1758), the title compound.

$^1$H nmr (CDCl$_3$, d$^6$ DMSO) δ: 7.70 (2H, d, J=9 Hz, aryl-H), 6.55 (2H, d, J=9 Hz, aryl-H), 4.25 (2H, brs, —NH$_2$), and 1.55 (9H, S, CH$_3$). Infra Red (Nujol mull) 3420, 3350, 3240, 1690, 1640, 1605, 1515, 1295, 1160, 1120, 850, 770, 700, and 615 cm$^{-1}$.

(b) t-butyl N-4-(N-2-phthalimidoethyl)aminobenzoate t-Butyl 4-aminobenzoate (1.93 g, 10 mmole) and N-(2-bromoethyl)phthalimide (2.54 g, 10 mmole) were heated together under nitrogen at 100° C. for 3¾ h. On cooling, the material was dissolved in dichloromethane (125 ml), filtered and evaporated to leave a yellow oil (3.35 g). This was chromatographed (30 g silica/dichloromethane) and the title compound (163 mg, 5%) isolated as a white solid. Recrystallisation from chloroform/petroleum ether (40°-60° C.) gave a solid m.p. 139°-141° C.

Found: C 69.70, H 6.14, N 7.71% $C_2H_2N_2O_4$ requires C 68.84, H 6.05 and N 7.65%. $^1H$ nmr (CDCl$_3$) δ: 7.6 (5H, m, aryl-H), 6.45 (2H, d, J=9 Hz, aryl-H), 4.5 (1H, br S, N—H), 3.9 (2H, t, J=6 Hz, $CH_2$ N=C=O), 3.4 (2H, m, $CH_2$NH) and 1.5 (9H, S, $CCH_3$). Infra Red (Nujol) 3370, 1775, 1705, 1685, 1610, 1525, 775 and 720 cm$^{-1}$.

(c) t-butyl N-4-(2-aminoethyl)aminobenzoate

The phthalimide produced above (240 mg) was dissolved in ethanol (10 ml) and hydrazine hydrate (40 μl) was added. The solution was heated to reflux overnight under nitrogen during which time a white precipitate was formed. Concentrated hydrochloric acid (150 μl) was added, and the solution cooled and filtered. The ethanol was removed by evaporation to leave an aqueous solution that was refiltered. The solution was basified with 15% sodium hydroxide solution and extracted with ethyl acetate (2×25 ml). The organic solution was dried (sodium sulphate), filtered and evaporated to leave a white crystalline compound (131 mg, 85%)—the desired diaminoester, m.p. 117°-119° C.

$^1H$ nmr (CDCl$_3$) δ: 7.75 (2H, d, J=9 Hz, aryl-H), 6.5 (2H, d, J=9 Hz, aryl-H), 4.55 (1H, brs, aryl-NH), 3,25 (4H, brs, $CH_2$), 1.55 (9H, S, $CCH_3$), and 1.4 (2H, brs, NH$_2$). Infra Red (Nujol): 3370, 1680, 1610, 1540, 1300, 1160, 930, 835, and 775 cm$^{-1}$. Found: C 65.94, H 8.55 and N 11.51%. $C_{13}H_{20}N_2O_2$ requires C 66.07, H 8.53 and N 11.85%.

(d) t-butyl
N-4-{N-2-[3-(2-pyridyldithio)propionyl]aminoethyl-}aminobenzoate t-Butyl N-4-(2-aminoethyl)-aminobenzoate (74 mg) and N-succinimidyl-3-(2-pyridyldithio)propionate (100 mg) were dissolved in dry pyridine (0.5 ml) and stirred overnight. The solvent was removed at reduced pressure and the residual gel was taken up in ethyl acetate (10 ml) and washed with a 10% aqueous sodium hydrogen carbonate solution (10 ml). The organic layer was dried (sodium sulphate), filtered and evaporated to yield an oil (131 mg, 96%), the title compound.

$^1H$ nmr (CDCl$_3$) δ: 8.25 (1H, m, aryl-H), 7.4 (6H, m, aryl-H+NHCO), 6.5 (2H, d, J=9 Hz, aryl-H), 4.65 (1H, brs, N—H), 3.4 (4H, m, CH$_2$NH), 3.05 (2H, t, J=6 Hz, $CH_2CO$), 2.60 (2H, t, J=6 Hz, CH$_2$—S—S), and 1.55 (9H, S, $CCH_3$). Infra Red (Neat) 3350, 3070, 1660, 1610, 1530, 1420, 1300, 1160, 1120, 910, 840, 770, 735 cm$^{-1}$.

(e)
N-4-{N-2-[3-(2-pyridyldithio)propionyl]aminoethyl-}aminobenzoic acid, bistrifluoroacetate salt The t-butyl ester (66 mg) was dissolved in trifluoroacetic acid (2 ml) and allowed to stand at room temperature for 90 minutes. The trifluoroacetic acid was removed at reduced pressure and the acid (90 mg) isolated as an orange oil in quantitative yield.

$^1H$ nmr (d$^6$ acetone/CDCl$_3$) δ:8.6 (1H, m aryl-H), 7.75 (5H, m, aryl-H), 6.65 (2H, d, J=9 Hz, aryl-H), 3.5 (4H, brs, NHCH$_2$), 3.05 (2H, t, J=6 Hz, COCH$_2$), and 2.65 (2H, t, J=6 Hz, $CH_2$ S).

(f) 4-amidinophenyl
N-4-{N-2-[3-(2-pyridyldithio)propionyl]aminoethyl-}aminobenzoate The acid bistrifluoroacetate (180 mg) was dissolved in pyridine (1 ml). 4-Amidinophenol (54 mg, 1 eq) was added followed by dichyclohexyl carbodiimide (64 mg, 1 eq). The solution went deep orange but this soon dissipated and dicyclohexyl urea was rapidly formed. After 5 h the solution was filtered through a plug of glass wool and pyridine was removed by evaporation to leave a brown oil (365 mg). Assuming complete esterification, this material was ~45% by weight the desired material and was contaminated by pryidinium trifluoroacetate.

Infra Red (Neat) 2400–3300, 1680, 1610, 1490, 1170, 840, 750 and 710 cm$^-$.

2-Chloro-4-amidinophenyl
N-4-{N-2-[3-(2-pyridyldithio)propionyl]aminoethyl-}aminobenzoate The acid bistrifluoroacetate (288 mg) was added to a solution of 2-chloro-4-amidinophenol (46 mg) in pyridine (1 ml). Dicyclohexylcarbodiimide (46 mg) was introduced. The material was stirred for 20 h, in which time a solid was precipitated. The material was filtered through a plug of glass wool, and the solvent removed by evaporation to leave a pale cream gum (288 mg). Assuming complete esterification, the product was about 45% pure by weight.

EXAMPLE 4

Active centre-linked conjugate of human tissue plasminogen activator with human serum albumin
(LINKER EXAMPLE 1)

(a) N-ε-(4-thiobutyrimino)-[LYSINE] human serum albumin

Human serum albumin (Kabi, 200 mg/m) was mixed with solid iminothiolane (Sigma, 10.3 mg) and incubated at pH 7.4, 37° C. for 1 h. The mixture was gel filtered into 3.5 ml 20% glycerol, 0.1M Tris.HCl, 0.9% w/v NaCl buffer (TGS) pH 7.4 using a small Sephadex G-25 M column at 4° C. Active site titration using Ellmanns Reagent (1.0 mM, 20% TGS, pH 7.4) gave a thiol content of 2.33 mM (2 determinations), corresponding to an average of 1.09 thiols/mol HSA. The solution was stored at −40° C.

(b)
N-ε-({2-[3-(4-butyriminodithio)propionyl]hydrazino} benzoic acid 4'-amidinophenyl ester.HCl)-[LYSINE] human serum albumin Thiolated albumin (VI, 1.5 ml) was mixed with the acylating agent of Example I(b) (10 mM in DMSO, 0.5 ml, 1.43 molar excess) and incubated at 0° C. for 60 min during which approximately 1.1 molar equivalents of pyridine 2-thione were released. Part of this material was subjected to two successive gel filtrations (Sephadex G-25 M) at 4° C. into 1% w/v D-mannitol, 20 mM ammonium bicarbonate, 1.0 mM 6-aminohexanoic acid (MAE) buffer, pH 7.4. Final vol: 3.5 ml, 1.05 mM ester. The solution was stored at −40° C.

(c) Coupling to human tissue plasminogen activator (t-PA)

Purified t-PA was mixed with 0.1M Trien.HCl pH 7.0 (0.5 ml) to give a final activity of 20,900 SU/ml and the above albumin ester (0.5 ml) added. On incubation at 0° C. amidolytic activity against S-2288 progressively decreased as illustrated in FIG. 1. The acylation process appeared to have two phases: one relatively rapid ($t_{\frac{1}{2}} \sim 13$ min) and the other slower ($t_{\frac{1}{2}} \sim 98$ min). Additional inactivation occured on freezing to $-40°$ C. and thawing. The product was mixed with a batch prepared under the same conditions but using $^{125}$I-MPA.

(d) Purification of the conjugate

A column (2×55 cm) of Sephacryl S-300 was calibrated by chromatography of a mixture of unmodified albumin and $^{125}$I-MPA (vial 5) in MAE buffer at 4° C. and a flow rate of 22 ml/h. Albumin and $^{125}$I eluted together at 62–88 ml. Crude conjugate chromatographed under the same conditions gave two peaks with apparent molecular weights greater than albumin and containing radioactivity. The fractions eluting at 42–64 ml were pooled and freezed-dried, yielding a white powder (244 mg). This process was repeated for several other batches.

(e) Deacylation of the conjugate

Freeze-dried batches of the conjugate were deacylated for pH 7.4, 37° C. in the above TGS buffer containing 0.01% w/v Tween 80 detergent. The average first order deacylation rate constant for four batches was about $4 \times 10^{-4}$ sec$^{-1}$. On prolonged storage, a slower component of deacylation characterised by a rate constant of about $5 \times 10^{-5}$ sec$^{-1}$ became evident and this correlated with an increase in the average molecular weight of the preparation (see below).

(f) Molecular weight of the conjugate

The size of the coupled products was examined by two techniques. First, polyacrylamide gel electrophoresis in the presence of sodium dodecyl sulphate (Laemmli, U.K. (1970), Nature, 277, 680) was used to separate the components of the conjugate which were detected either by autoradiography of the $^{125}$I-t-PA or by the fibrin overlay zymography (Granelli-Piperno, A. & Reich, E. (1978), J. Exp. Med., 148, 223) which detects fibrinolytic enzymes. Secondly, size exclusion high performance liquid chromatography with calibrated modified silica columns was used to separate the conjugate mixture before and after deacylation. All these methods gave similar results which may be summarised as follows:

(1) t-PA-associated radioactivity and enzymatic activity is associated with several species with a molecular weight in the range 130 to 900 kilodaltons. The individual components correspond to conjugates of t-PA with one, two, three etc (up to at least 10) albumin units.

(2) All the discrete conjugate proteins appeared to possess fibrinolytic activity after deacylation. Treatment of the conjugate with TGS buffer or 0.5M hydrazine pH 8.0 at 37° C. for several hours resulted in the liberation of an active component (separable by HPLC or SDS-PAGE) with equimolar weight corresponding to unmodified t-PA (65–70 kilodaltons).

(g) Clearance of the conjugate from the bloodstream of rats (See also: Methods)

Figure 2:
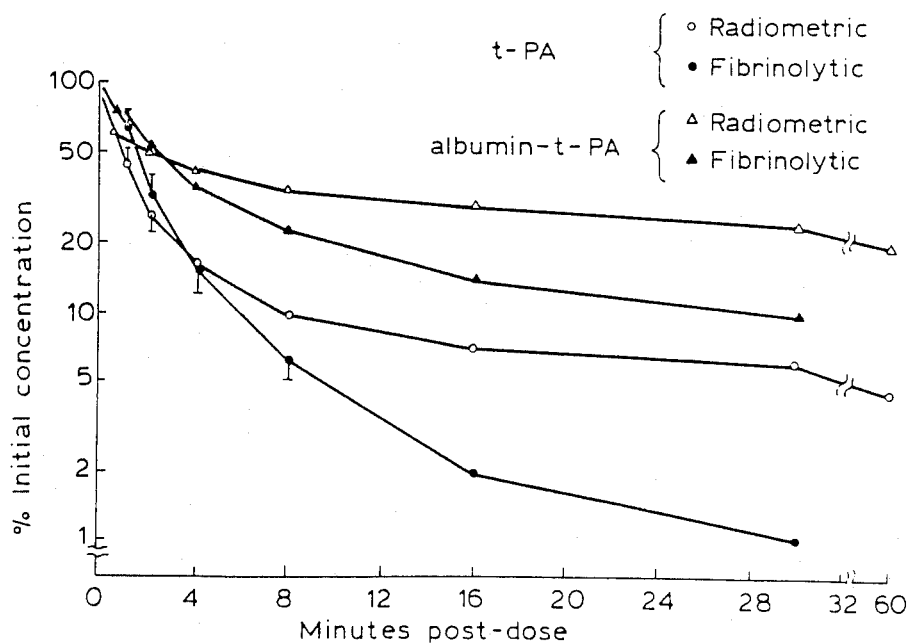
FIG. 2 shows the clearance of unmodified t-PA and of the albumin-t-PA conjugate of Example 4.

The rate of removal of unmodified t-PA and of albumin-t-PA conjugate from the circulation of rats was measured by both radiometric and fibrinolytic methods. The results are shown in FIG. 2. The activity of unmodified t-PA was removed very rapidly ($t_{\frac{1}{2}}$ about 1.5 min). Radiometric measurements diverged from activity measurements after c. 8 min, probably because of recycling of metabolised $^{125}$I-label into the bloodstream. Both the enzyme activity and the radioactivity of the albumin conjugate were cleared significantly more slowly than the unmodified enzyme, with part of the dose being cleared with an apparent half-life of about 36 min. Integration of the concentration/time plots for the two agents suggests that the conjugate had at least a 10-fold greater bioavailability than the unmodified t-PA. Since the conjugate gives rise to unmodified t-PA by hydrolysis, it can therefore function as a slow-release form of the fibrinolytic agent in vivo.

EXAMPLE 5

Active centre-linked conjugate of human tissue-plasminogen activator with human serum albumin (linker example 2)

Human serum albumin (Kabi, 200 mg/ml, 10 ml) was mixed with 2-iminothiolane (4.1 mg:1 mole equivalent) and incubated at 25° C. for 75 min. Titration with Ellmann's reagent showed a concentration of 2.82 mM thiol after this time. An aliquot of this solution (0.5 ml) was mixed with the acylating agent of Example 2(b) (70 µl of 20 mM in DMSO, 1 molar equivalent) and held on ice for 1 h. t-PA (50,000 SU) and tracer $^{125}$I-t-PA (960,000 c.p.m.) were added. The mixture slowly decreased in activity over 72 h at 0° C. although the decrease could be accelerated by incubation at 25° C. for short periods of time. The final amidolytic activity was 37% of the initial level. The product was applied to a column (300×22.5 mM) of TSK-G-3000 SW modified silica gel and subjected to high performance gel permeation chromatography. The buffer used was 0.08M sodium phosphate, 0.32M sodium chloride, 20% v/v ethanol pH 7.0 (Buffer H, Hefti, F. (1982) Anal. Biochem., 121, 378–381) at a flow rate of 1.0 ml/min at 22° C. Four peaks of protein-bound radioactivity were observed, the first near the void volume of the column (40 ml) was of very high molecular weight material, the second at about 58 ml was of material with MW>200 kilodaltons. The third peak eluted at about 64 ml and corresponded to MW around 130 kilodaltons. Unmodified t-PA eluted at about 74 ml. A pool of eluate from 52–66 ml was collected, gel filtered into MAE buffer (diluted 1:5 v/v in water and containing 1 mg/ml human serum albumin) and freeze-dried. This yielded 81 mg of a white solid. Radiochemical yield: 16.5%. Deacylation of this material in TGS buffer containing 0.01% w/v Tween 80, at 37° C. showed that it contained initially about 14% uncoupled t-PA and that this rate constant for deacylation was about $6.4 \times 10^{-5}$ sec$^{-1}$.

Figure 3:
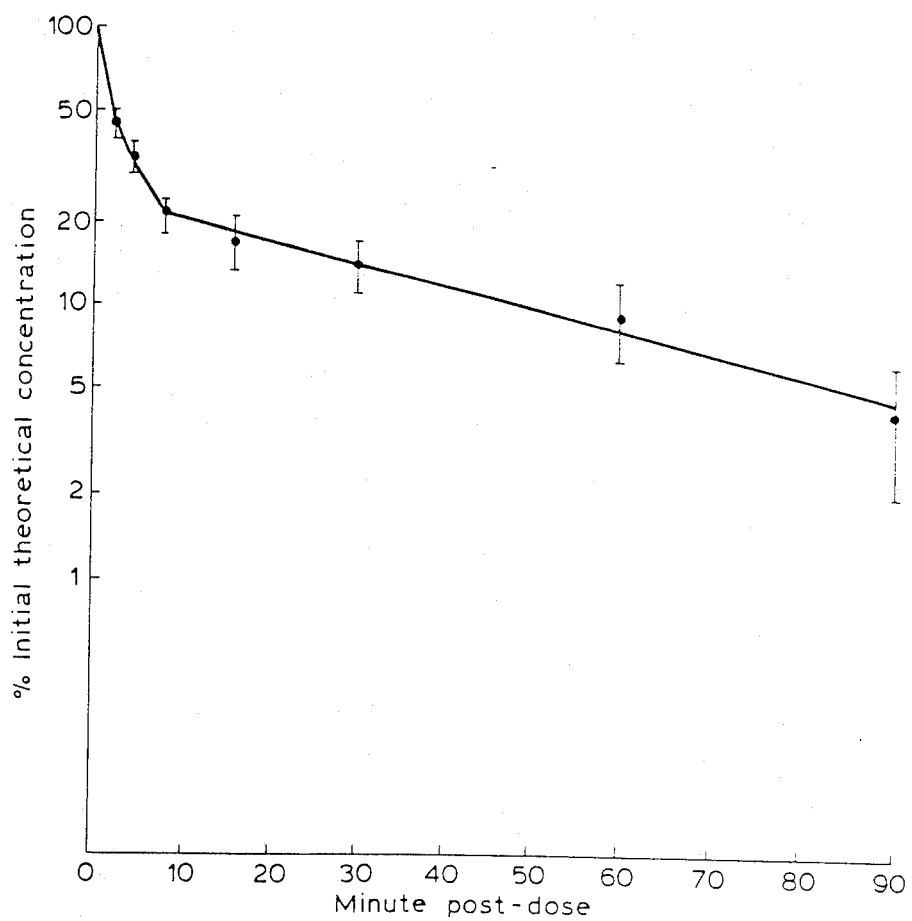
FIG. 3 shows the clearance of the albumin-t-PA conjugate of Example 5.

This material was injected into rats at a dose of 2000 SU/kg and the fibrinolytic activity in the bloodstream determined as described in method (c). FIG. 3 shows the clearance of the conjugate (2000 SU/kg) from the bloodstream of rats (n=5). A slow phase of clearance with a half-life of about 36 min could be identified. Comparison with FIG. 2 shows that this clearance is appreciably slower than that of unmodified t-PA.

EXAMPLE 6

Active-centre linked conjugate of human tissue plasminogen activator with human immunoglobulin G (linker example 1)

(a) N-ε-4-thiobutyrimino[lysine]human immunoglobulin G

Human immunoglobulin G (Sigma, 100 mg) was dissolved in degassed 50 mM sodium phosphate 0.1M sodium chloride pH 7.4 buffer (PBS buffer, 1.0 ml) and 2-iminothiolane (50 μl of a fresh 50 mM solution in PBS) added. The mixture was incubated at 37° C. for 1 h and then gel filtered on a small Sephadex G-25 column into 3.4 ml of PBS at 4° C. The product was used immediately.

(b) N-ε-({2-[3-(4-butyriminodithio)propionyl]hydrazino} benzoic acid 4'-amidinophenyl ester.HCl)-[lysine]human immunoglobulin G The above thiolated IgG was mixed with the acylating agent of Example 1(b) (85 μl of 20 mM in DMSO) and incubated at ambient temperature (22°-24° C.) for 10 min. Cold (−20° C.) ethanol (10 ml) was added with mixing over 30 sec. The mixture was centrifuged at 18,000 g for 30 min at 4° C. and the pellet redissolved in PBS buffer (3.4 ml). Saturated ammonium sulphate solution (10 ml) was added with mixing over 1 min and the centrifugation repeated. The pellet was dissolved in 2.2 ml PBS and gel filtered into 3.4 ml of the same buffer at 4° C. The product was used immediately.

(c) Coupling to human tissue plasminogen activator (t-PA)

Purified t-PA (approx. 26 nmoles) was mixed with the product of step (b) to give a solution containing 51,000 SU/ml. The mixture was held on ice for 24 h after which the residual activity was 11,600 SU/ml (22.7%). The product was centrifuged to remove small amounts of insoluble material and an aliquot (50 μl) diluted into TGS buffer containing 0.01% w/v Tween 80. The deacylation of this sample was measured at 37° C. and gave a first order constant of about $5.7 \times 10^{-4}$ sec$^{-1}$. The remaining product was stored in solution at −70° C. and showed a high molecular weight (c-200 Kilodaltons) fibrinolytic component (susceptible to hydrolysis) when analysed by fibrin overlay zymography.

EXAMPLE 7

Active-centre-linked conjugate of human tissue-plasminogen activator with human serum albumin (linker example 3)

(a) 4-{N-2-(3-[2-pyridyldithio]propionyl)aminoethylamino}benzoyl human tissue-plasminogen activator Tissue-plasminogen activator (46 nmoles in 3.0 ml 0.1M sodium 4-guanidinobutyrate pH 7.4 was treated with the acylating agent of Example 3f (30 μl of 50 mM in DMSO) at 4° C. for 16 h and then at 25° C. for 5 h. After this time, 4.6% of the initial amidolytic activity remained. 2.5 ml of this solution was gel filtered into 3.5 ml of TGS buffer containing 0.01% w/v Tween 80. Dilution of an aliquot of this solution 1:20 v/v into TGS/Tween 80 and deacylation at 37° C. indicated that the first order deacylation rate constant was about $6.6 \times 10^{-4}$ sec$^{-1}$. The remaining solution was used immediately.

(b) Coupling to thiolated human serum albumin

Human serum albumin (Sigma, 200 mg) was dissolved in PBS (0.1 ml) and incubated for 1 h at 25° C. with 60 μl of 50 mM fresh aqueous 2-iminothiolane. The product was gel filtered into PBS (3.5 ml) and the filtrate immediately mixed with the above acyl-t-PA solution. After holding at 0° C. for 30 min, the product was stored frozen at −40° C.

SDS-PAGE/fibrin overlay zymography of the product demonstrated the presence of high molecular weight fibrinolytic components which were susceptible to hydrolysis.

EXAMPLE 8

A conjugate of urokinase linked to the active centre of human plasmin (linker example 1)

(a) Preparation of thiolated urokinase

High molecular weight urokinase (Serono 500,000 IU, 32.8 nmoles) was mixed with tracer $^{125}$I-UK ($1.13 \times 10^6$ c.p.m.) in PBS buffer (1.0 ml) and treated with 2-iminothiolane (25 μl of a 50 mM solution in cold (0° C.) water). The mixture was incubated at 25° C. for 75 min and gel filtered (Sephadex® G-25) into MAE buffer diluted 1:1 v/v with water (3.5 ml). This solution was freeze-dried.

(b) 4-(3-{2-pyridyldithio}propionyl)hydrazio benzoyl (Ser-740) human plasmin

Lys-plasminogen (100 mg) was dissolved in TGS buffer (1.0 ml) and activated with urokinase (5000 IU) at 0° C. for 2 h. The resulting plasmin had an activity of $3.7 \times 10^6$ SU/ml and was treated with the acylating agent of Example 1 (50 μl of a 20 mM solution in DMSO) for 1 h at 0° C. After this time, the amidolytic activity was reduced to 0.6% of the initial level and the mixture was gel filtered into MAE buffer (3.4 ml) and freeze-dried in 0.2 ml aliquots. One aliquot was reconstituted in PBS buffer (3.0 ml) and reduced with dithiothreitol (5 mM). The increase in optical density at 343 nM attributable to release of pyridine-2-thione indicated that each aliquot contained approximately 27 nmoles of acyl-enzyme. The first order deacylation rate constant of the product was about $1.96 \times 10^{-4}$ sec$^{-1}$.

(c) Coupling of the components

The above urokinase was mixed with 5 aliquots of acyl-enzyme in PBS buffer (1.0 ml) and held at 0° C. for 2 h. Approximately 61 nmoles of pyridine 2-thione were released as measured spectrophotometrically. The product was purified by preparative high performance gel permeation chromatography as described in Example 5. The conjugate eluted at around 60-68 ml and this pool was gel filtered into MAE buffer (diluted 1:1 v/v with water and containing 1 mg/ml human serum albumin and freeze-dried in 6 aliquots). Unmodified urokinase eluted from the column at around 78 ml. The final yield of conjugate was 8.3% (radiochemical) or 9.6% (amidolytic). Hydrolysis of the conjugate at 37° C. for 45 min in TGS buffer indicated release of plasmin as measured by a 4-fold increase in amidolytic activity against the plasmin substrate S-2251. SDS PAGE and fibrin overlay zymography revealed components corresponding to one and two molecules of acyl plasmin conjugated to each UK molecule. The high MW bands were sensitive to hydrolysis in TGS buffer at 37° C. for 3 h.

EXAMPLE 9

A conjugate of p-aminobenzoyl urokinase linked to the active centre of human plasmin (linker example 2)

Urokinase (Serono 500,000 IU, 32.8 nmoles) was mixed with tracer $^{125}$I-UK $(1.70 \times 10^6$ c.p.m.) and treated with 2-iminothiolane (13.3 μl of 10 mM in cold water) in PBS buffer (0.5 ml) at 25° C. for 75 min. This product was used without further processing. 2-(N-6-[3-{2-pyridyldithio}propionyl]aminohexylaminobenzoyl (Ser-740) human plasmin was prepared by reacting plasmin (prepared as in Example 8(b), 0.9 ml) with the acylating agent of Example 2(b) (80 μl of 20 nM in DMSO) for 2 h at 25° C. The amidolytic activity of the plasmin decreased to 8.8% of the inital activity under these conditions. The product was gel filtered into MAE buffer, diluted 1:5 v/v in water (3.2 ml) and freeze-dried in 4 aliquots. Reduction of one of these aliquots with dithiothreitol indicated an acyl-enzyme content of about 140 nmoles. The above thiolated urokinase was mixed with 4-aminobenzoic acid 4'-amidinophenyl ester.HCl (20 μl of 50 nM solution in DMSO) and added to 1 vial of acyl-plasmin. The mixture was incubated at 25° C. for 40 min and then chromatographed using the HPLC conditions described in Example 4. Monitoring the radioactivity of the effluent showed that the conjugate eluted between 59 and 66 ml whereas unmodified urokinase appeared around 75-79 ml. The former pool was gel filtered into MAE buffer diluted 1:5 v/v in water (10.2 ml) and freeze-dried in aliquots. Deacylation of one of these aliquots in TGS buffer at 37° C. indicated a first order deacylation rate constant for removal of the p-aminobenzoyl group at the urokinase active site of about $2.7 \times 10^{-4}$ sec$^{-1}$. The acyl group linking the urokinase to the plasmin was much more stable ($k < 2 \times 10^{-5}$ sec$^{-1}$). SDS-PAGE and fibrin overlay zymography showed a pattern similar to that noted for Example 8.

Figure 4:
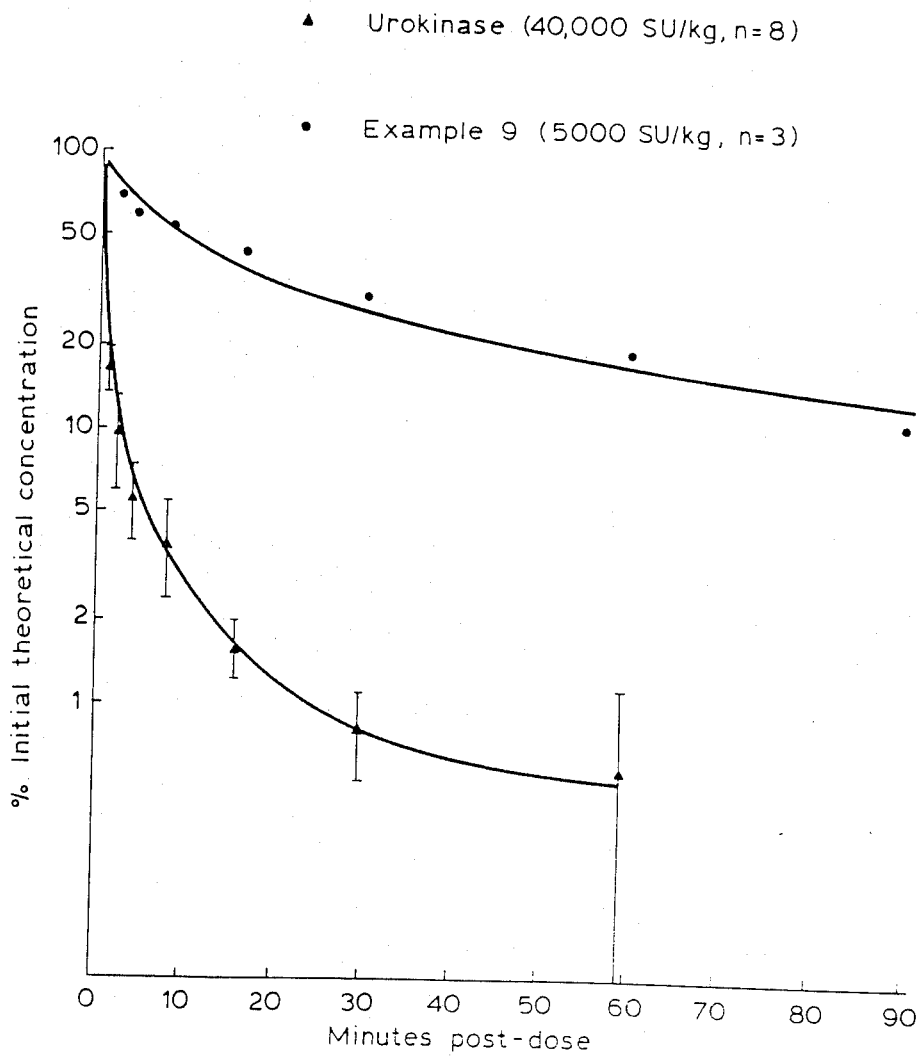
FIGS. 4 and 5 show the clearance of unmodified urokinase and of the plasmin-urokinase conjugate of Example 9.
Figure 5:
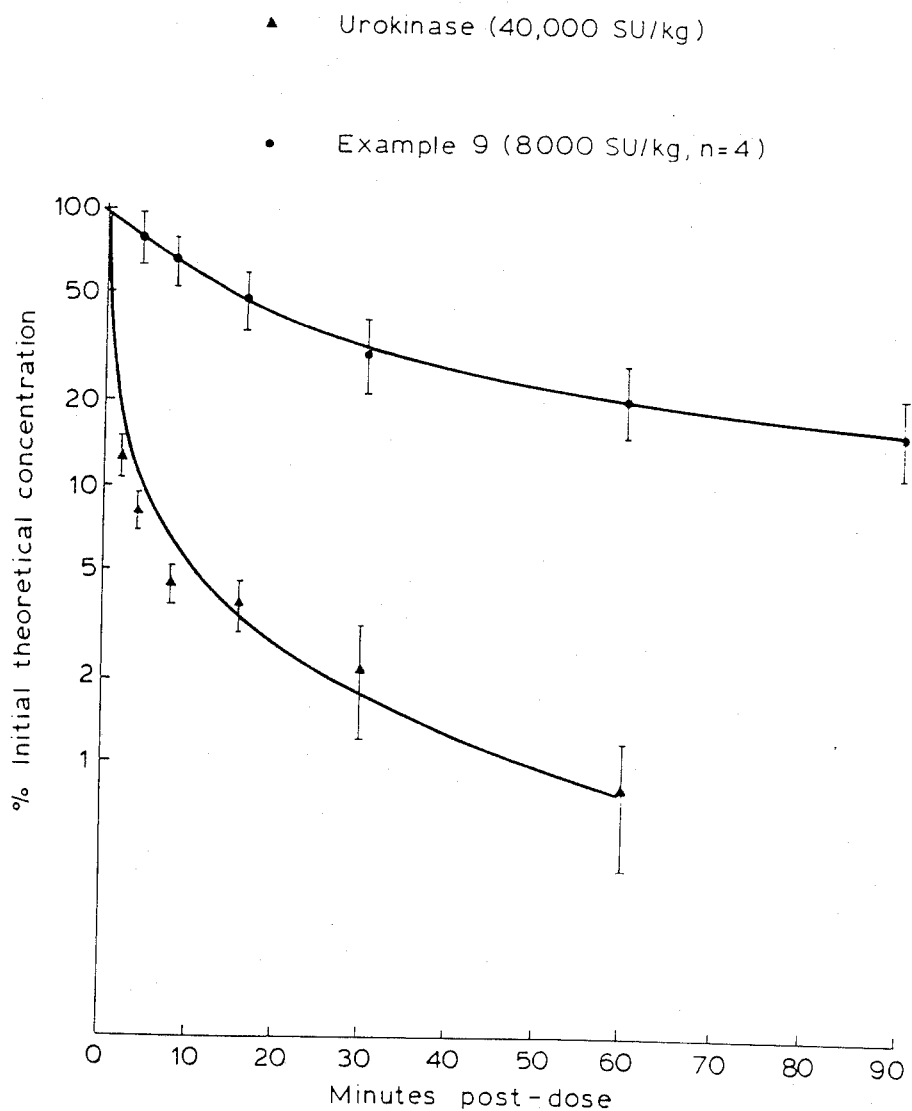

The compound was injected into 4 rats (at 8,000 SU/kg i.v.) and the clearance of fibrinolytic activity from the bloodstream measured using the technique described in Method (c) and compared with the clearance of unmodified urokinase (at 40,000 SU/kg). FIG. 4 shows the results obtained using euglobulin precipitation. An extended plasma half-life of 33-47 min compared with unmodified UK was observed. The clearance of this agent was also studied in guinea pigs (Method (e) at a dose of 5,000 SU/kg i.v. FIG. 5 compares the clearance of unmodified UK and the conjugate and shows that a half-life of 40-50 min applies to at least 50% of the injected conjugate dose in marked contrast to the more rapid clearance of UK itself.

EXAMPLE 10

A conjugate of urokinase linked to the active site of human plasmin (linker example 3)

(a)
4-{N-2-(3-[2-pyridyldithio]propionyl)aminoethylamino}benzoyl human plasmin (method 1)

Human plasmin solution was prepared by the method of Example 8(b) and had an amidolytic activity of $3.05 \times 10^6$ SU/ml. 1.5 ml of this solution was mixed with the acylating agent of Example 3(f) (75 μl of a 50 mM solution in DMSO). The mixture was incubated at 4° C. for 16 h, at 25° C. for 2 h and, after a further 75 μl of acylating agent had been added, at 37° C. for 30 min. The amidolytic activity was then reduced to 1.16% of the initial level. The product was filtered through a 0.22μ filter and purified by HPLC using the conditions described for Example 5. The acyl plasmin eluted between 62 and 68 ml and was well separated from excess acylating agent. The acyl-plasmin pool was gel filtered into MAE buffer (9.6 ml) and freeze-dried in 6 aliquots. Reduction of one such aliquot with dithiothreitol indicated an acyl-anzyme content of 5.62 nmoles/aliquot. Deacylation of the acyl-enzyme in TGS/Tween 80 buffer at 37° C. gave a first order deacylation rate constant of about $6.4 \times 10^{-5}$ sec$^{-1}$.

(b) Coupling to thiolated urokinase

High molecular weight urokinase (Serono, 500,000 IU, 32.8 nmoles) was mixed with tracer $^{125}$I-UK $(1.33 \times 10^6$ c.p.m.) in PBS buffer containing 0.01% w/v Tween 80 (1.0 ml) and mixed with 2-iminothiolane (50 μl of 50 mM fresh in cold water), followed by incubation at 25° C. for 1 h. The product was gel filtered into PBS/Tween 80 (3.5 ml) and immediately added to 5 vials of the above acyl-plasmin (28.1 nmoles) and 0.2 ml of a 44 μM solution of bovine lung trypsin inhibitor (aprotinin). The mixture was placed in a Centricon ™ centrifugal ultrafiltration vial and centrifuged at 4° C. for 2 h at 5000 g. This process reduced the volume to 1.1 ml. The product was purified by HPLC using the conditions described for Example 4. Three peaks of radioactivity were observed: the first at about 56 ml corresponded to a conjugate of MW~200 kilodaltons, the second at about 64 ml to material of 100-140 kilodaltons and the third at 80-82 ml to unmodified urokinase. The first two peaks (pools: 52-58 ml, 60-68 ml) were gel filtered into MAE buffer and freeze-dried. The radiochemical yield of the high MW fraction (corresponding to urokinase coupled to 2 plasmin molecules) was 6.3% and that of the second fraction (a 1:1 conjugate) was 9.8%. The recovery of amidolytic activity in the two fractions was 3.9 and 11% respectively. SDS-PAGE/fibrin overlay zymography confirmed the presence of high MW conjugate bands in the two fractions.

EXAMPLE 11

A conjugate of human tissue-plasminogen activator linked to the active centre of human plasmin (linker example 1)

Tissue-plasminogen activator (18,000 SU) mixed with tracer $^{125}$I t-PA $(2 \times 10^6$ c.p.m.) in PBS buffer containing 0.01% w/v Tween 80 (2.5 ml) was treated with 2-iminothiolane (25 μl of 50 mM in cold PBS/Tween) and the mixture incubated at 25° C. for 30 min. The product was gel filtered into PBS/Tween buffer (3.0 ml) and mixed with one aliquot of the acyl-plasmin of Example 8(b) and aprotinin solution (20 μl of 44 μM). The mixture was incubated on ice for 1 h. SDS-PAGE/fibrin overlay zymography of this material revealed a high MW conjugate band which was sensitive to hydrolysis.

EXAMPLE 12

Active centre linked conjugate of tissue-plasminogen activator with human plasminogen (linker example 1)

Human lys-plasminogen (1.2 ml of a 9.4 mg/ml solution in PBS buffer containing 33% v/v glycerol) was mixed with 2-iminothiolane (24 μl of a fresh 50 mM solution in water) and incubated at 37° C. for 4 min. The acylating agent of Example 1(b) (150 μl of a 10 mM solution DMSO) was added and the mixture held on ice for 1 h. The product was gel filtered (Sephadex ™ G-25) into PBS buffer containing 1.0 mM 6-aminohexanoic acid (3.2 ml). Part of the resulting thiolated plasminogen solution (1.0 ml) was mixed with t-Pa (20,000) and tracer $^{125}$I-t-PA ($1 \times 10^6$ c.p.m.) and incubated at 0° C. After 2½ h, the amidolytic activity of the t-PA was decreased to 7.7% of the initial level. Part of the product was subjected to HPLC separation on a modified silica gel column (TSK G-3000, 600×7.5 mM) in Buffer H (see Example 5) at 0.5 ml/min and 22° C. A high molecular weight peak of radioactivity eluted at about 17 ml and unmodified t-PA eluted at about 20 ml. SDS-PAGE/fibrin zymography also revealed the presence of a hydrolysis-sensitive high MW fibrinolytic component.

EXAMPLE 3

A conjugate of human tissue-plasminogen activator linked to the active centre of human plasmin (linker example 3)

Tissue-plasminogen activator (78 nmoles in 3.4 ml 0.1M sodium 4-guanidinobutyrate, 0.3M sodium chloride, 20 mM sodium phosphate, 0.01% w/v Tween 80 pH 7.4) was treated with 50 μl of 50 mM 2-iminothiolane (fresh in cold water) at 25° C. for 70 min. 1.7 ml of this solution was gel filtered into 3.4 ml of the above buffer on Sephadex ™ G-25. Titration of the thiol groups in the t-PA with Ellmann's reagent indicated an average of about 0.6-0.7 moles of thiol/mole of protein. The thiolated t-PA was mixed with aprotinin (132 nmoles), the above buffer (0.4 ml) and the acyl-plasmin of Example 10(a) (53 nmoles). The mixture was concentrated in Centricon ™ vials to a final volume of 1.0 ml (5000 g/4° C. for 2 h). The product contained about 23 nmoles of t-PA as measured by amidolytic assay. Analysis of the product by SDS-PAGE/fibrin overlay zymography showed that a fibrinolytically active component with an apparent molecular weight of about 150 kilodaltons was present together with unmodified t-PA. Reduction of this material with dithiothreitol (c. 20 mM at 0° C. for 30 min) removed most of the high molecular weight component, thus confirming that the components of the conjugate were linked by a disulphide bridge.

EXAMPLE 14

A conjugate of urokinase linked to the active centre of human plasmin (linker example 2, no acylation of the active centre of urokinase)

High MW urokinase (Serono, 500,000 UI, 32.8 nmoles) was dissolved in PBS buffer containing 0.01% w/v Tween 80 (1.0 ml) and treated with 25 μl of 50 mM 2-iminothiolane at 25° C. for 1 h. The product was gel filtered into MAE buffer and freeze-dried. Ellmann's titration showed that the average thiol content of the modified UK was 0.8 moles/mole. The product (64 nmoles) was mixed with N-2-[N-6-{3-(2-pyridyldithio)-propionyl}aminohexyl]aminobenzoyl (SER 740) human plasmin prepared as in Example 9 (330 nmoles) in PBS/Tween buffer (1.0 ml) and held at 0° C. for 4 h. The product was partially purified by HPLC on a modified silica gel column (TSK G-4000 SW, 7.5×600 mM) in buffer H at a flow rate of 1.0 ml/min at 25° C. The product eluting between 20 and 24 ml was gel filtered into MAE buffer containing 1 mg/ml human serum albumin and freeze-dried. 151 g of white solid resulted and part of this (81 mg) was repurified on a column (16×200 mm) of Sephacryl ™ S-300 in 4 mM ammonium bicarbonate, 0.1% w/v D-mannitol at a flow rate of 10 ml/h at 4° C. Two fractions were collected and freeze-dried. The first corresponded to high molecular weight material (42–52 ml) and the second to material around 90 kilodaltons in MW (54–62 ml). SDS-PAGE/fibrin overlay zymography showed that the high MW fraction contained a fibrinolytically active component at around 220 kilodaltons (UK linked to 2 plasmin molecules) as well as the conjugate of UK with one plasmin (134 kilodaltons) and free UK. Like the conjugate of Example 9, the product was not easily hydrolysed.

What is claimed is:

1. A compound of the formula (II):

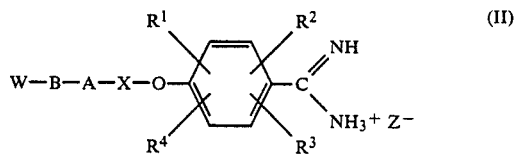

wherein B is a hydrophilic linking group; A is a bridging group comprising one or two heteroatoms independently selected from the group consisting of oxygen, sulphur and nitrogen, in which the nitrogen is unsubstituted or substituted by alkyl of 1 to 6 carbon atoms; X is an optionally substituted benzoyl group further substituted at the 2- or 4-position by the moiety A, and optionally substituted acryloyl group joined to A at the 2- or 3-position or a naphthoyl group; and W is a group capable of reacting directly with the amino acid side chain of a protein or with a protein attachment group to produce a covalent bond between B and said side chain or attachment group; Z is a counter anion; and $R^1$, $R^2$, $R^3$ and $R^4$ are ach hydrogen or an electron withdrawing moiety which increases the reactivity of an amidinophenyl ester.

2. The compound according to claim 1, which is 4-[N-2-(3-[2-pyridyl]dithiopropionyl)hydrazino]benzoic acid 4'-amidinophenyl ester.

3. The compound according to claim 1, which is N-(6-[3-(2-pyridyl)dithiopropionyl]aminohexyl)anthranilic acid 4'amidinophenyl ester.

4. The compound according to claim 1, which is 2-chloro-4-amidinophenyl N-4-(N-2-[3-(2-pyridyldithio)propionyl]aminoethyl)aminobenzoate.

5. A compound according to claim 1, wherein A is

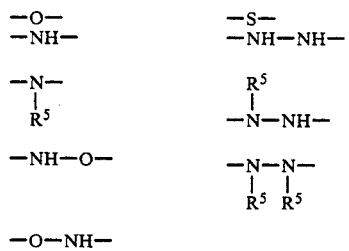

wherein $R^5$ is alkyl of 1 to 6 carbon atoms.

6. A compound according to claim 1, wherein B is a substituted alkane of 2 to 10 carbon atoms or a linear polymer.

7. A compound according to claim 1, wherein B is a —S(CH$_2$)$_2$CONH—, —S—(CH$_2$)$_2$CONH(CH$_2$)$_6$— or —S—(CH$_2$)$_2$CONH(CH$_2$)$_2$—.

8. The compound according to claim 1, which is 4-amidinophenyl N-4-(N-2-[3-(2-pyridyldithio)propionyl]aminoethyl)aminobenzoate.

9. The compound according to claim 1, wherein W is pyridylthio or 2-nitro-4-azido phenyl.

* * * * *